(12) United States Patent
Howlett

(10) Patent No.: US 6,341,603 B1
(45) Date of Patent: Jan. 29, 2002

(54) INHALATION APPARATUS

(75) Inventor: David John Howlett, King's Lynn (GB)

(73) Assignee: Bespak plc (GB)

( * ) Notice: Subject to any disclaimer, the term of this patent is extended or adjusted under 35 U.S.C. 154(b) by 0 days.

(21) Appl. No.: 09/458,048

(22) Filed: Dec. 10, 1999

(30) Foreign Application Priority Data

Dec. 11, 1998 (GB) ................................................ 9827404

(51) Int. Cl.[7] .............................................. A61M 11/00
(52) U.S. Cl. ............................. 128/200.23; 128/200.12
(58) Field of Search ....................... 128/200.23, 203.12, 128/203.15, 203.21, 200.21, 200.22, 205.24, 200.11–200.14, 200.18, 200.24; 604/58

(56) References Cited

U.S. PATENT DOCUMENTS

| | | | | |
|---|---|---|---|---|
| 5,027,808 A | * | 7/1991 | Rich et al. | 128/203.23 |
| 5,060,643 A | * | 10/1991 | Rich et al. | 128/200.23 |
| 5,069,204 A | * | 12/1991 | Smith et al. | 128/200.23 |
| 5,119,806 A | * | 6/1992 | Palson et al. | 128/200.14 |
| 5,184,761 A | * | 2/1993 | Lee | 222/402.2 |
| 5,408,994 A | * | 4/1995 | Wass et al. | 128/203.15 |
| 5,447,150 A | * | 9/1995 | Bacon | 128/200.14 |

FOREIGN PATENT DOCUMENTS

EP 0 476 991 9/1991

\* cited by examiner

Primary Examiner—John G. Weiss
(74) Attorney, Agent, or Firm—Smih, Gambrell & Russell LLP

(57) ABSTRACT

This invention relates to dispensing apparatus for use with pressurised dispensing containers and in particular, but not exclusively, for apparatus for dispensing orally inhaled medicinal products in aerosol forms. The apparatus comprises a housing (4) adapted to receive a pressurized dispensing container (2) and a mouth piece (11). Valve means (28) is provided, moveable between a first position in which a duct is closed and a second position in which a duct is open, and a flow sensor being activatable, by means of an air flow created when a user applies suction to the mouth piece, to move the valve means (28) into its second position. Wherein the flow sensor comprises a diaphragm (60) and the diaphragm and/or housing is provided with at least one aperture (64), wherein the diaphragm comprises a first element (66) connected to the housing and a second element (62) axially slidably moveable relative thereto. The first and second diaphragm elements being connected by a flexible member (61).

11 Claims, 8 Drawing Sheets

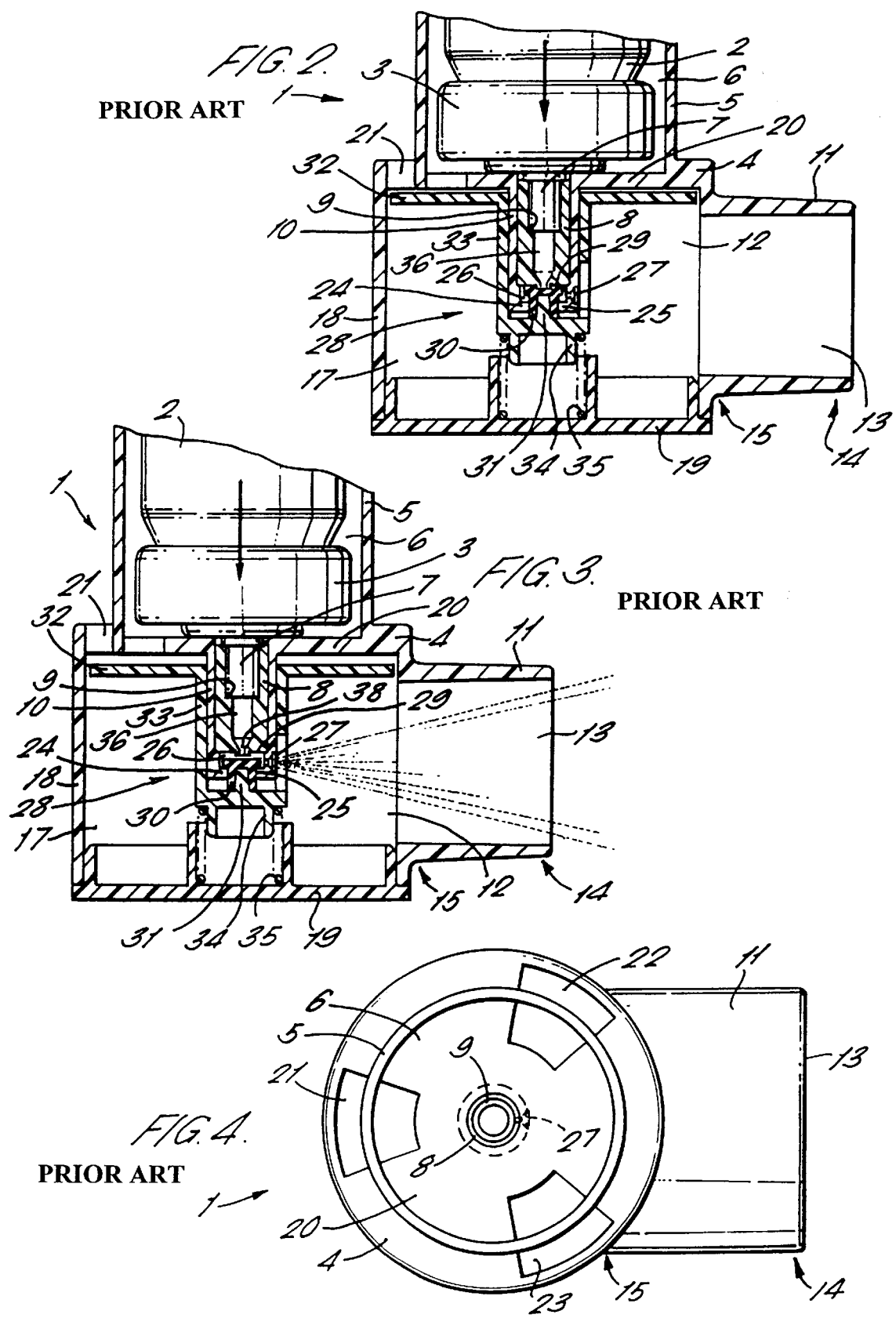

INHALATION APPARATUS

FIELD OF THE INVENTION

This invention relates to dispensing apparatus for use with pressurised dispensing containers and in particular, but not exclusively, for apparatus for dispensing orally inhaled medicinal products in aerosol form.

BACKGROUND OF THE INVENTION

Various means have been proposed to synchronise the release of an aerosol product into a mouthpiece of a dispensing apparatus in a manner which is synchronised with the inhalation of breath by a user. Such synchronisation is important in ensuring that as much as possible of the dispensed dose reaches the lungs of the user. This is of particular importance when administering drugs for the relief of asthma.

It has been proposed in GB 1392192 to provide a pivoted vane mechanism to sense air flow and release the aerosol product as a result of the user's inspiratory effort. Such a mechanism is difficult to manufacture to the required tolerance for controlled and repeatable performance in oral inhalation due to difficulties in moulding and distortions appearing in the moulded elements. There remains a need to provide a practical solution which will be suitable for production on a commercial scale.

It is known from U.S. Pat. No. 4,576,157 to provide dispensing apparatus comprising a housing defining a socket for receiving, in use, a pressurised dispensing container of the type having a tubular valve stem biassed into an extended position and having first valve means operable to dispense fluid through the stem when the stem is depressed. The housing defines an airway extending from an inlet means, which is open to the atmosphere, to an outlet defined by a mouthpiece. Inhalation by a user results in an air flow through the airway. The apparatus further comprises an actuator, in which the stem is sealingly received in use such that the actuator and the stem together define a first chamber into which fluid is dispensable by operation of the first valve means. A second valve means normally closes the chamber and is actuatable to release fluid from the first chamber to flow into the airway. The second valve means comprises a valve member located externally of the first chamber and co-operable with a valve seat of the actuator. A flow sensor is arranged in the airway and operable to actuate the second valve means in response to a flow of air being sensed in the airway. The flow sensor is movable in response to the flow of air in a bore defined by the housing between first and second positions corresponding to closed and open conditions of the second valve means respectively. The flow sensor is connected directly to the valve member and provided with biassing means urging the flow sensor into the first position, in which the valve member is biassed into sealing contact with the valve seat.

It is further known from EP 0476991 to provide a dispensing apparatus in which a flow sensor is provided comprising a piston, which is axially movable in the bore, and guide means operable to guide the movement of the piston so as to maintain a lateral surface of the piston in spaced relationship from a side wall of the bore. A passageway is thus defined having a cross-section which is substantially uniform throughout the travel of the piston between the first and second positions. The passageway, constituting a constricted portion of the airway, presents a substantially uniform impedance to the flow of air throughout the movement of the piston. As the user inhales, a pressure drop is developed across the flow path. This pressure drop acts on the piston to define a force which is used to operate the device.

An advantage of this arrangement is that the user experiences a constant impedance to the inhaled air flow throughout the inhalation process resulting in a slow and steady flow of air in which the atomised medicament is carried. Such a characteristic of flow rate has proved to be highly beneficial to the effective deposition of inhaled medicaments where deposition of an atomised spray in the user's lungs is intended. In contrast, any discontinuity in the flow rate resulting from a change in impedance can result in a rapid increase in flow rate with consequent early deposition of the medicament in the throat or mouth of the user. A further advantage is that the uniformity of flow avoids any "dead spot" in the flow characteristic during which the user is prevented from receiving inhaled air, thereby avoiding unnecessary distress for the user who may for example be an asthmatic.

A disadvantage of this arrangement has been found to be the significant variability in the cross-section of the air passageway due to typical manufacturing tolerances. For example, the external diameter of the piston may be typically 30.00 mm+/−0.10 mm and the internal diameter of the bore typically 30.60 mm+/−0.10 mm. Thus, the minimum surface area of the air flow passageway might be 19.04 $mm^2$ and the maximum surface area 38.08 $mm^2$. This represents a variability of +/−33% approximately. Such variability in the cross-sectional area of the air flow passageway results in variability of the force available for operating the apparatus.

SUMMARY OF THE INVENTION

According to the present invention there is provided inhalation apparatus for dispensing a product comprising a housing adapted to receive a pressurised dispensing container, and a mouthpiece, a duct for conveying, in use, product from the container to the mouthpiece, valve means movable between a first position in which the duct is closed and a second position in which the duct is open, and a flow sensor being activatable, by means of an airflow created when a user applies suction to the mouthpiece, to move the valve means into its second position, wherein the flow sensor comprises a diaphragm and the diaphragm and/or housing is provided with at least one aperture, wherein the diaphragm comprises a first element connected to the housing and a second element axially slidably movable relative thereto, the first and second diaphragm elements being connected by a flexible member.

In one embodiment the diaphragm comprises at least one aperture.

In another embodiment the housing comprises at least one aperture.

In another embodiment at least one aperture is provided in the second diaphragm element.

Optionally a trigger extends from an exterior of the apparatus into contact with the diaphragm such that operation of the trigger moves the diaphragm axially.

Preferably the trigger is rotatably pivoted on the housing such that one end protrudes through an aperture in the housing and the other end contacts the diaphragm.

Preferably the apparatus further comprises an actuator having a projection, the diaphragm being connected to a tubular guide portion which is axially slidable on a guide surface of the projection to facilitate movement of the diaphragm.

The actuator further defines an actuator chamber, valve seat and outlet nozzle, the tubular guide portion comprising a spigot on which a valve member of the valve means is mounted.

In one embodiment the housing comprises a socket for receiving the pressurised dispensing container, the housing defining at least one port communicating between the socket and the mouthpiece at a location upstream of the diaphragm with respect to the direction of air flow during inhalation.

Typically a pressure drop of between 2.5 and 4 KPa is developed across the diaphragm when an airflow of 50 liters/minute is created by suction on the mouthpiece.

The present invention also provides dispensing means comprising inhalation apparatus in combination with a pressurised dispensing container; said container having a tubular valve stem biased into an extended position and having valve means operable to dispense a metered dose of product through the valve stem when the valve stem is depressed

BRIEF DESCRIPTION OF THE PREFERRED EMBODIMENTS

Embodiments of the present invention will now be described by way of example only and with reference to the accompanying drawings of which:

FIG. 2 is a sectional side elevation of a part of the dispensing apparatus of FIG. 1 in which the pressurised dispensing container has been depressed to actuate a first valve means;

FIG. 3 is a sectional side elevation of a part of the dispensing apparatus of FIG. 1 in which the dispensed product is released into a flow of inhaled air;

FIG. 4 is a plan view of the dispensing apparatus of FIGS. 1 to 3, with the pressurised dispensing container omitted;

Figure 9:
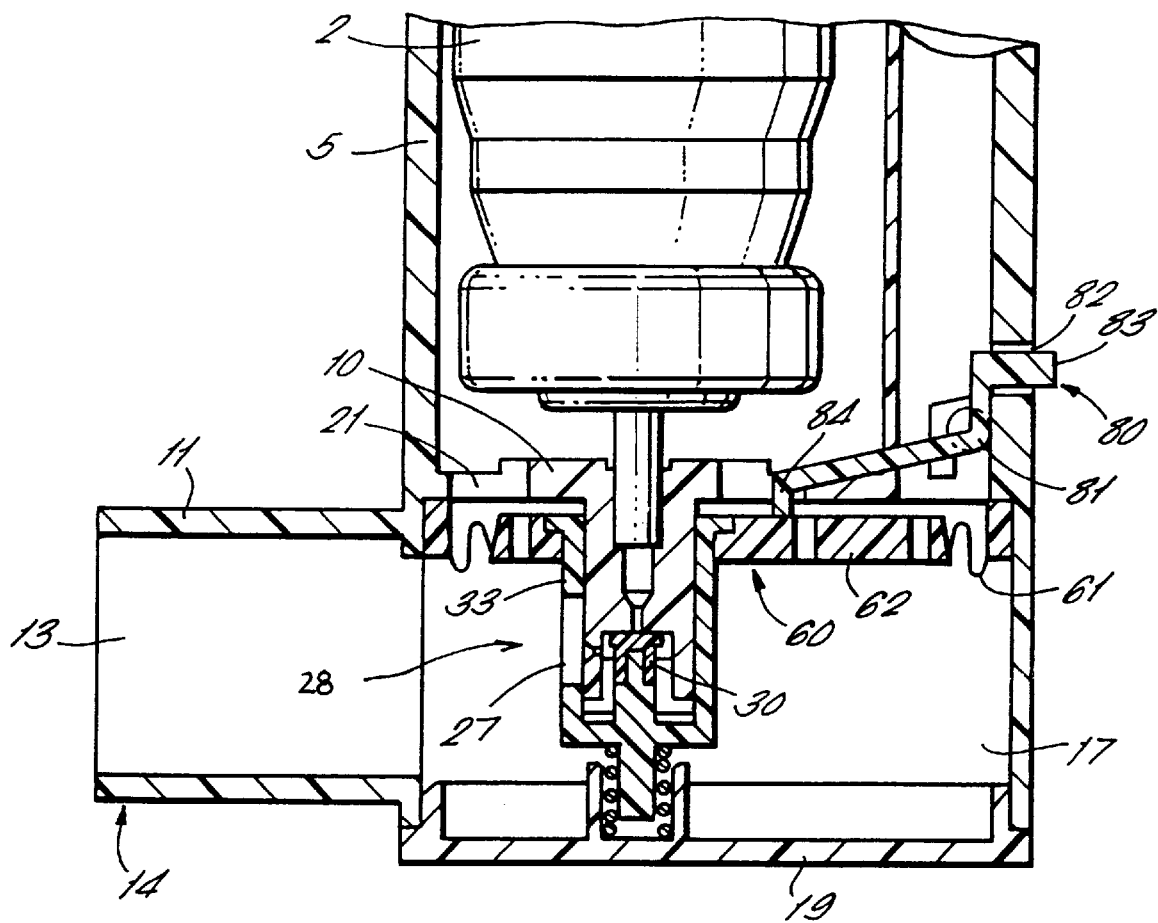
Figure 10:
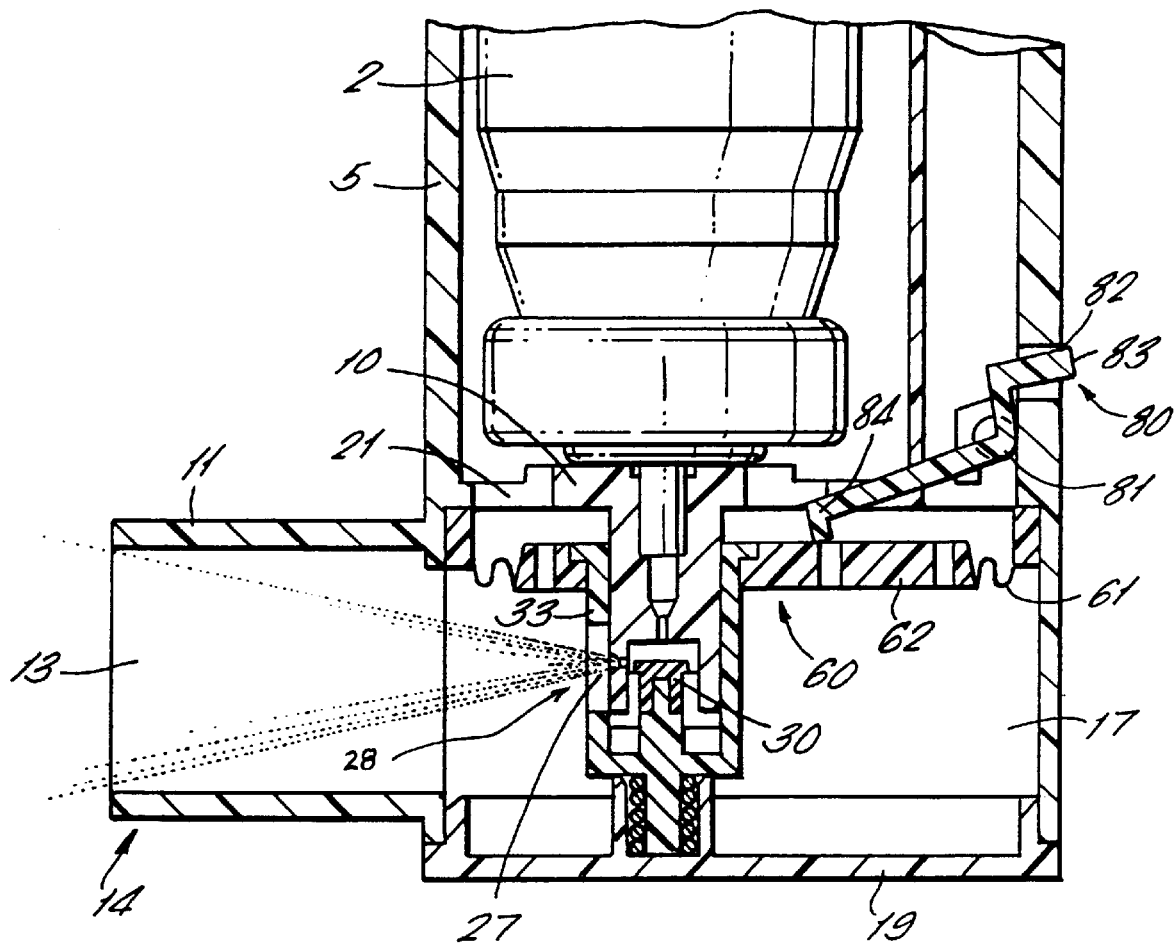

FIG. 9 is a sectional side elevation of a part of the dispensing apparatus in accordance with a third embodiment of the present invention, including a pressurised dispensing container, the apparatus being in a first, non-dispensing position; and FIG. 10 is a sectional side elevation of a part of the dispensing apparatus of FIG. 9, including a pressurised dispensing container, the apparatus being in a second, dispensinq position.

DETAILED DESCRIPTION

Figure 1:
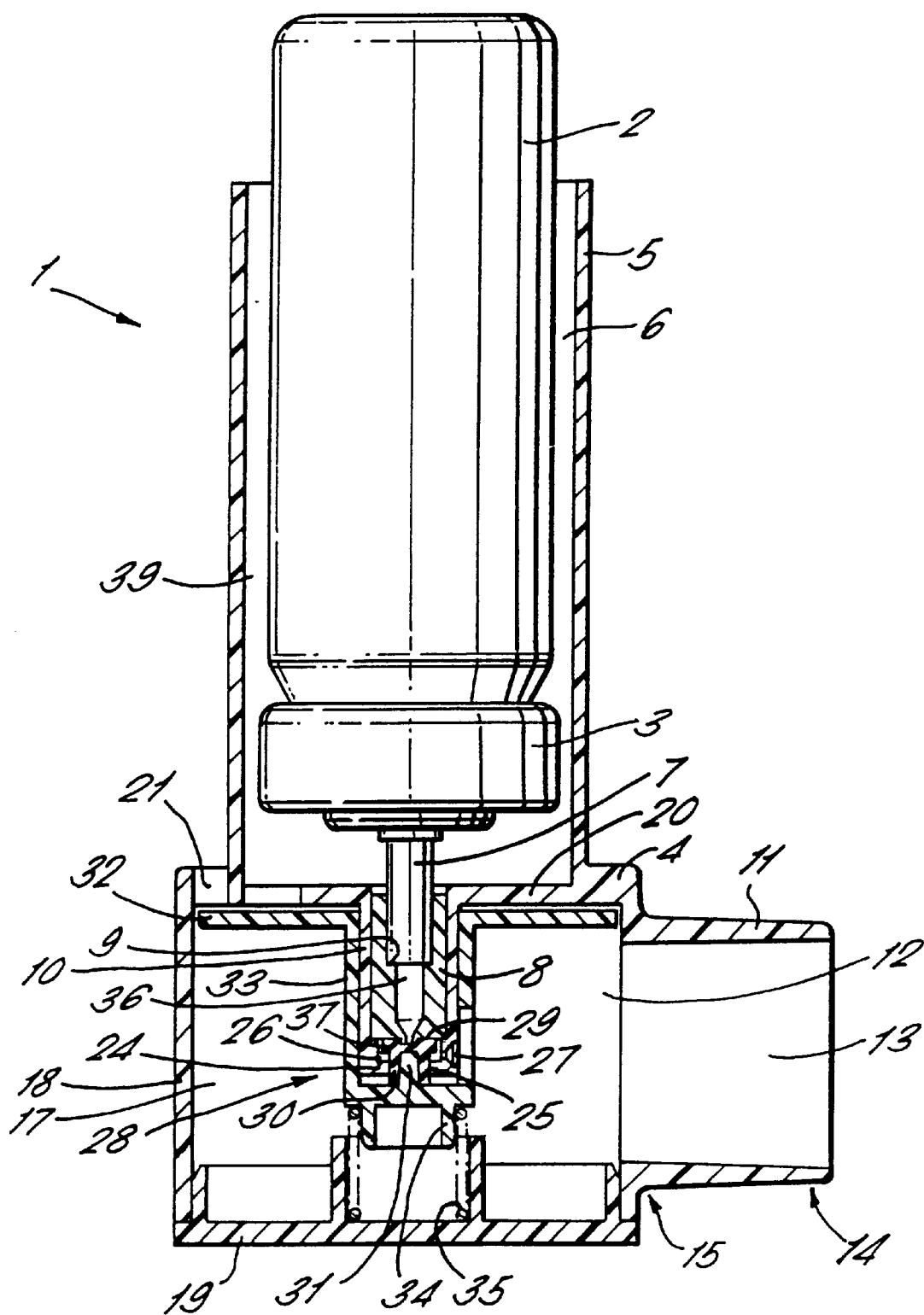
FIG. 1 is a sectional side elevation of a prior art dispensing apparatus, including a pressurised dispensing container.

FIGS. 1 to 4 depict a dispensing apparatus of known type. In FIG. 1 the dispensing apparatus 1 is shown in combination with a pressurised dispensing container 2 with the apparatus oriented so as to be ready for use in an orientation in which the pressurised dispensing container extends vertically with valve 3 lowermost. The pressurised dispensing container 2 contains a product such as a liquid medicament mixed with a volatile propellant liquid.

In the following description, the reference to vertical and horizontal orientation of components of the apparatus 1 refer to orientations of such components when the apparatus is held in its normal working orientation shown in FIG. 1.

The apparatus comprises a housing 4 which includes an upwardly projecting cylindrical portion 5 defining a cylindrical recess or socket 6 in which the dispensing container 2 is axially and slidably received. The container 2 is a loose fit in the socket 6 such that air can freely flow through the socket through a peripheral space 39 between the container and the socket.

The housing 4 further comprises a mouthpiece 11 defining a horizontally extending air duct 12 communicating with an outlet orifice 13 at a first end 14 of the mouthpiece. A second end 15 of the mouthpiece 11 communicates with a chamber 17 in the bottom of the housing 4.

A tubular valve stem 7 projects downwardly from the pressurised dispensing container 2. The container has a valve 3 located internally of the container 2, which are actuated by axial depression of the valve stem 7 against internally provided spring bias to dispense a metered dose of product through the valve stem 7.

The valve stem 7 is received sealingly in a bore of a tubular actuator 8. The bore includes an annular shoulder 9 which acts as a stop limiting the extent to which the valve stem 7 extends within the actuator 8.

The actuator 8 is received as a snug fit within a downwardly extending tubular member 10 formed integrally with the housing 4.

The chamber 17 is closed by a cap 19. A wall 20 separates the cylindrical portion 5 and chamber 17. The wall 20 is provided with three circumferentially equispaced inlet ports 21, 22 and 23 allowing air to enter the chamber 17, from the peripheral space 39 in the cylinder socket 6 and from the exterior of the housing. The outlet orifice 13 is of oval cross-section so as to be comfortably received in the mouth of a user.

The air duct 12 extends from the inlet ports 21, 22 and 23 through the chamber 17 and the mouthpiece 11 to the outlet orifice 13.

The tubular member 10 has an end wall 24 defining an aperture 25 communicating with an annular space 26 formed between the end wall 24 and the actuator 8. A nozzle 27 defined by the tubular member 10 communicates with the annular space 26 and is oriented to release fluid from the annular space into the chamber 17 in a direction towards the outlet orifice 13.

A piston 32 is vertically slidably received in the chamber 17, to which is attached a substantially tubular guide 33 which is co-axially mounted on the tubular member 10 and is slidable thereon. A boss 34 projects downwardly from the guide 33 and a helical compression spring 35 is located on the boss 34 and extends into contact with the wall 19 so as to bias the piston 32 upwardly. A spigot 31 projects upwardly from an end wall of the piston tubular element.

An actuator valve 28 is formed in the tubular projection 10 by an annular valve seat 29 at the lower end of the actuator 8 and a resilient valve member 30 which extends from the bore 17 into the annular space 26 and is normally urged into sealing contact with the valve seat 29 by a spigot 31. The valve member 30 has a cylindrical body which is recessed to accommodate the spigot 31 as an interference fit so that the spigot 31 and valve member 30 are connected sufficiently firmly to enable the valve member 30 to be positively unseated from the valve seat when the spigot is retracted. The valve member 30 is recessed so as to be penetrated by the spigot 31 which is received as an interference fit thereby firmly attaching the valve member to the spigot 31. The valve member 30 is a sliding fit within the aperture 25 and is provided with a radially projecting flange 37 of greater diameter than the aperture 25 so that the flange 37 acts as a stop limiting downward motion of the valve member 30 through the aperture 25.

The piston 32 is shown in FIGS. 1 and 2 in its normal rest position in which it lies adjacent the housing wall 20. Its diameter is such that a restricted flow of air is allowed from the inlet ports 21, 22 and 23 into the chamber 17. Typically, the piston 32 is of 30.00 mm diameter and the chamber 17 is dimensioned to provide a clearance of 0.30 mm between each side of the piston 32 and chamber 17. A restricted annular air passageway is thereby defined between the piston 32 and walls of the chamber 17. The ports 21, 22 and 23 are, in contrast, dimensioned to provide a greater cross-sectional area for the passage of air.

The actuator 8 and the hollow tubular valve stem 7 together define an actuator chamber 36 which, in use, is closed at its upper end by the container valve 3 and, at its lower end, by the actuator valve 28.

In use, a user holds the housing 4 with the cylindrical portion 5 oriented vertically as illustrated in FIGS. 1 to 4, and inserts the mouthpiece 11 into their mouth. The user depresses the pressurised dispensing container 2 relative to the housing 4 so as to actuate the container valve 3. Actuation of the container valve 3 results in a metered dose of pressurised product entering the actuator chamber 36, which is closed off by the actuator valve 28. The user then inhales through the mouthpiece 11, thereby reducing the air pressure within the housing chamber 17. The piston 32 is subjected to a downward force because of an imbalance of air pressure above and below the piston since the air pressure above the piston 32 is maintained at ambient air pressure via the inlet ports 21, 22 and 23. The piston 32 is thereby urged downwardly against the spring bias of spring 35. As the piston 32 moves downwardly, the spigot 31 on the tubular guide 33 also moves downwardly thereby unseating the resilient valve member 30 from the valve seat 29 so that the pressurised product escapes from the actuator chamber 36 into the annular space 26. As the product begins to escape, dissolved propellant in liquid form boils off from the dispensed dose causing the escaping product to rapidly expand. This expansion assists in further displacing the valve member 30 away from the seat 29. Displacement of the valve member 30 away from the seat is limited by engagement between the flange 37 and the end wall 24 of the tubular member 10. Fluid pressure acting on the valve member 30 provides sealing action between the flange 37 and the end wall 24 so that pressurised fluid cannot escape through the aperture 25. The pressurised fluid within the annular space 26 then escapes via the nozzle 27 as shown in FIG. 3. The piston 32 thereby constitutes a flow sensor which detects the flow of air in the duct 12 and which enables the second valve means 28 to be actuated to dispense the metered dose in synchronisation with the inhalation of air.

Air is drawn during inhalation through the air duct 12 via the inlet ports 21, 22 and 23 and passes peripherally around the piston 32 into the chamber 17 and thereafter is inhaled through the mouthpiece 11. The product dispensed through the nozzle 27 is mixed with the inhaled air and is administered to the lungs of the user.

Releasing the manual pressure on the pressurised dispensing container 2 allows it to resume its normal position, as shown in FIG. 1, and at the end of inhalation the piston 32 and guide 33 return to their rest positions as shown in FIG. 1 under action of the spring 35. The dispensing apparatus 1 is then ready for re-use.

The mouthpiece may be provided with a cover (not shown) to prevent the ingress of debris when the apparatus 1 is not in use.

The apparatus 1 may also optionally include a mechanism for retaining the container 2 in its depressed condition throughout the dispensing operation. This is advantageous where the container valve 3 is of a type which vents to atmosphere the internal bore of the valve stem when the container valve 3 is in the closed condition. It is therefore important for the container 2 to remain depressed relative to the housing 4 until after the valve means 28 has been actuated to dispense the dose into the inhaled air.

Figure 5:
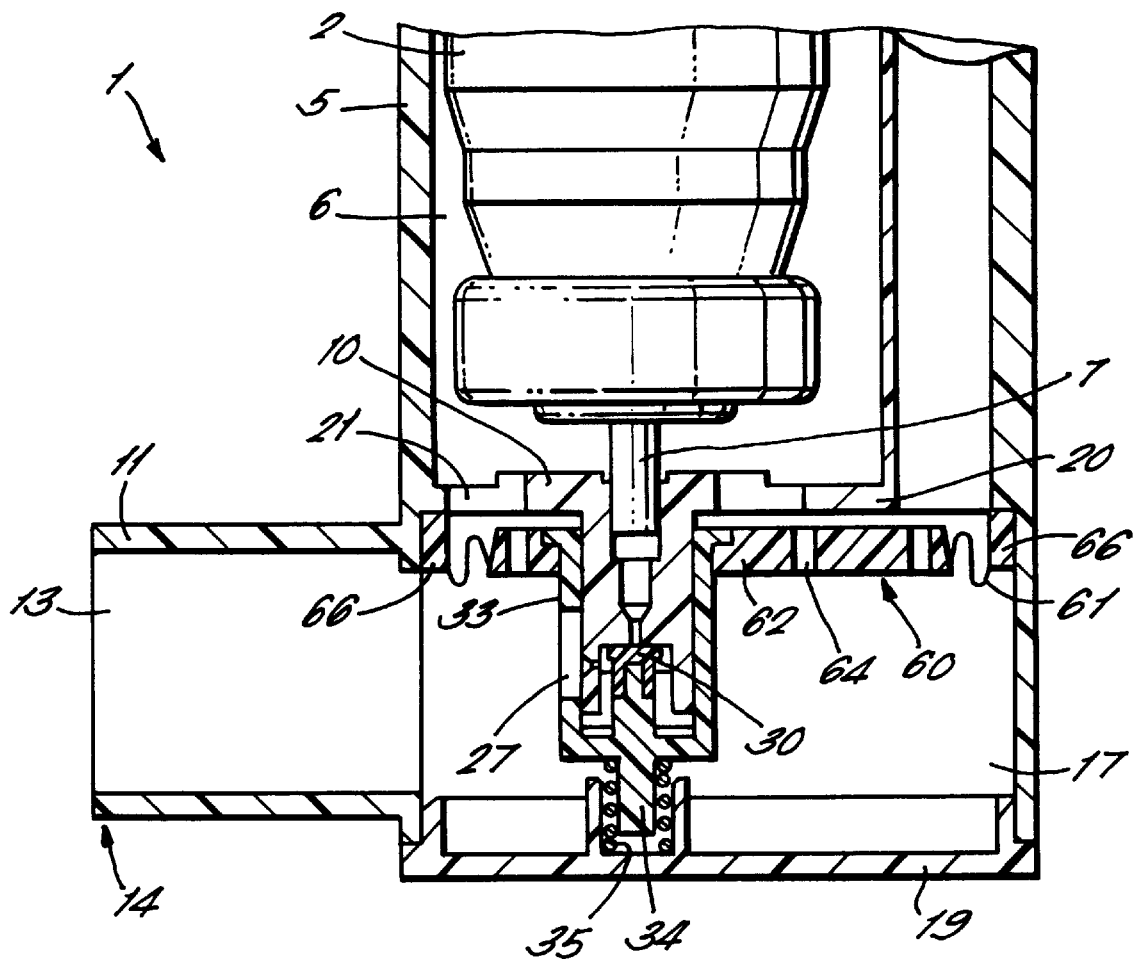
FIG. 5 is a sectional side elevation of a part of the dispensing apparatus in accordance with a first embodiment of the present invention, including a pressurised dispensing container, the apparatus being in a first, non-dispensing position.
Figure 6:
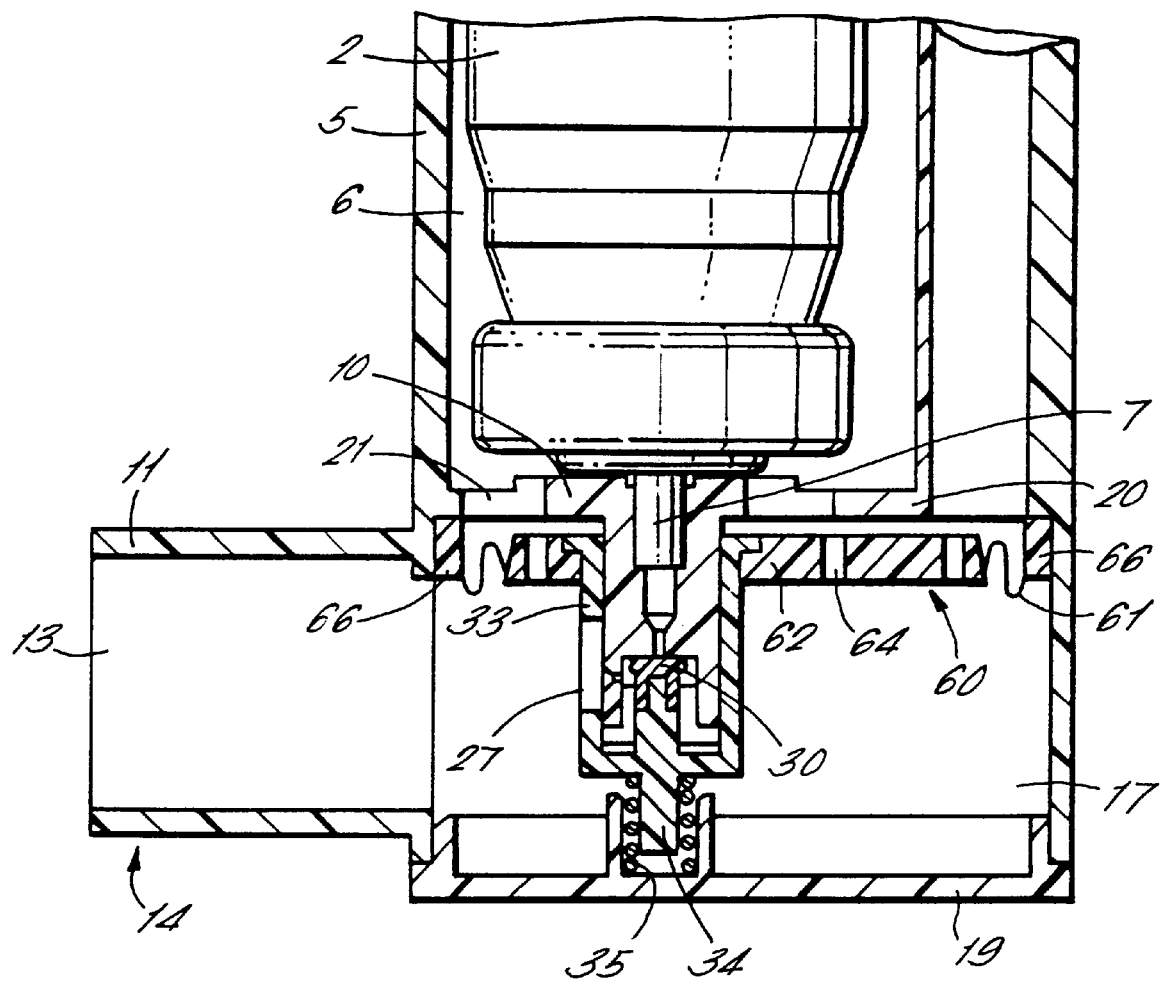
FIG. 6 is a sectional side elevation of the part of the dispensing apparatus of FIG. 5, the apparatus being in a second, intermediate position.
Figure 7:
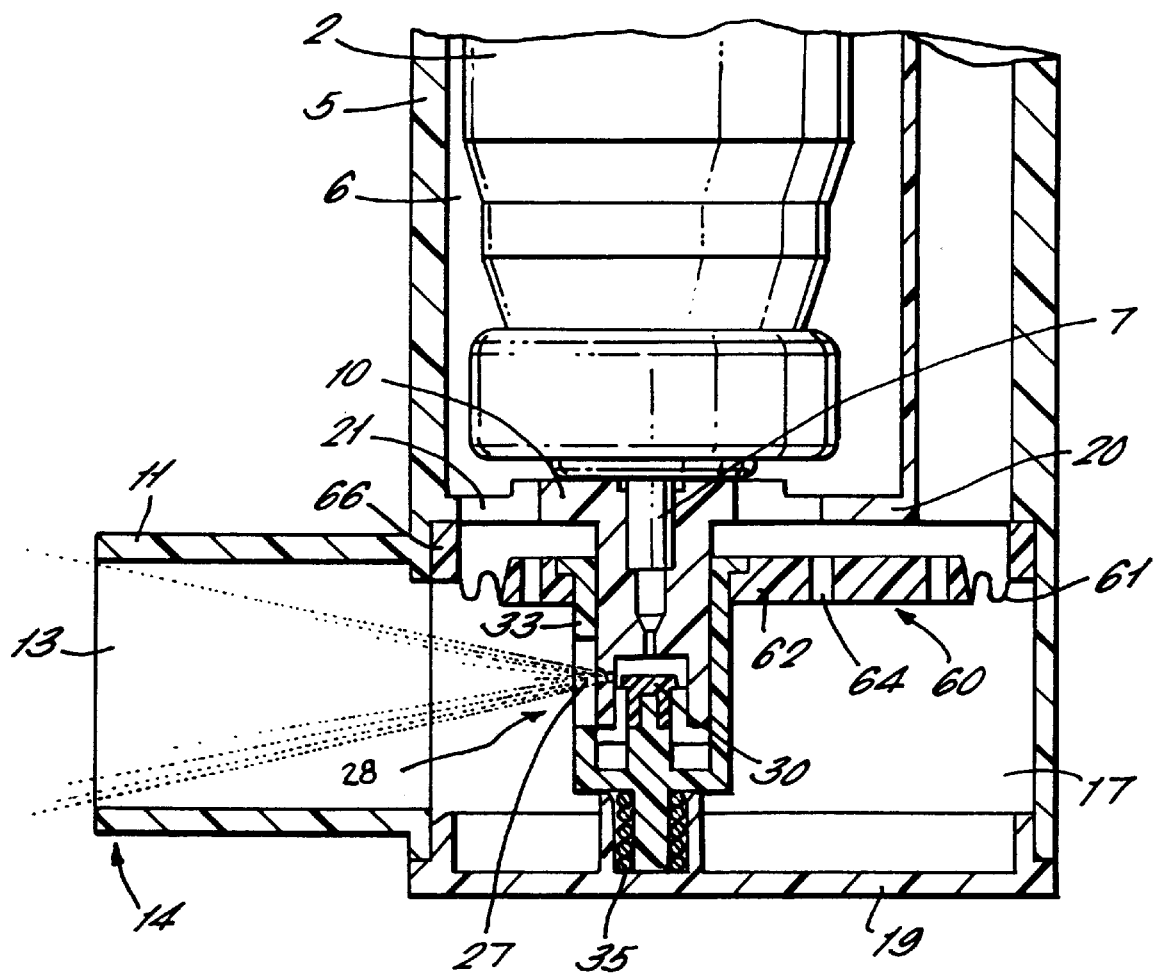
FIG. 7 is a sectional side elevation of the part of the dispensing apparatus of FIG. 5, the apparatus being in a third, dispensing position.

FIGS. 5 to 7 show a first embodiment of dispensing apparatus according to the present invention. Those components of like design and function to components of the prior art embodiment of FIGS. 1 to 4 have been given like reference numerals.

In the first embodiment of the present invention, piston 32 is replaced by a substantially annular diaphragm, generally depicted by reference 60. The diaphragm 60 comprises two essentially rigid elements. A first is a ring-shaped element 66 which is attached to the fixed body of the apparatus adjacent the housing wall 20. The second is an annular element 62 which extends laterally across chamber 17. The first and second elements 66, 62 of the diaphragm 60 are connected by a flexible member 61, preferably in the form of a rolling seal which allows vertical displacement of the second diaphragm element 62 relative to the first diaphragm element 66, whilst maintaining an air tight seal therebetween. The second diaphragm element 62 is attached to the tubular guide 33 which, as in the prior art, is co-axially mounted on the tubular projection 10 and slidably thereon. A boss 34 projects downwardly from the guide 33 and a helical compression spring 35 is located on the boss 34 and extends into contact with the cap 19, so as to bias the tubular guide 33 and second diaphragm element 62 upwardly.

The second diaphragm element 62 is provided with a number of apertures 64, say, four holes of equal diameter.

It has been found that significantly greater control over the variability of the area of the air flow passageway may be achieved by the use of apertures in such a rolling diaphragm 60 compared to the use of a chamber 17 and concentric piston 32. For example, if each of four holes has a diameter of 2.80 mm manufactured to a tolerance of +/−0.05 mm, the maximum cross-sectional area of the air flow passageway equals 25.52 mm$^2$ and the minimum area equals 23.75 mm$^2$. Thus, the variability is only approximately +/−3% to 4%. This is significantly less than the +/−33% variability of the prior art devices.

In use, the device of the present invention functions similarly to the device of FIGS. 1 to 4. FIG. 5 shows the apparatus prior to inhalation by the user. As the user inhales orally through the mouthpiece 11 it is the second diaphragm element 62 which is subjected to a downward force because of an imbalance of air pressure above and below the diaphragm 60. As a result, the second diaphragm element 62 is urged downwardly against the biasing of the spring 35.

Downward movement of the second diaphragm element 62 and tubular guide 33 results in actuation of the cylinder valve means 30, as shown in FIG. 6, and then the second valve means 28 as shown in FIG. 7 and as described in the prior art embodiment of FIGS. 1 to 4.

It has been found that the best results in use of inhalation apparatus is obtained where the user of the apparatus feels some resistance to breathing when they start to inhale. As a result it has been found beneficial to make the air flow passageway as restricted as practical since this results in a higher pressure drop across the diaphragm. As a result a smaller diaphragm may be used to create the necessary operating force. This allows the overall dimensions of the dispensing apparatus to be minimised. In practice it has been found that the best results are obtained where the size and positioning of the air flow apertures 64 is such that a pressure drop of between 2.5 and 4 KPa is developed across the diaphragm when operated at a typical flow rate of 50 liters/minute of air.

Figure 8:
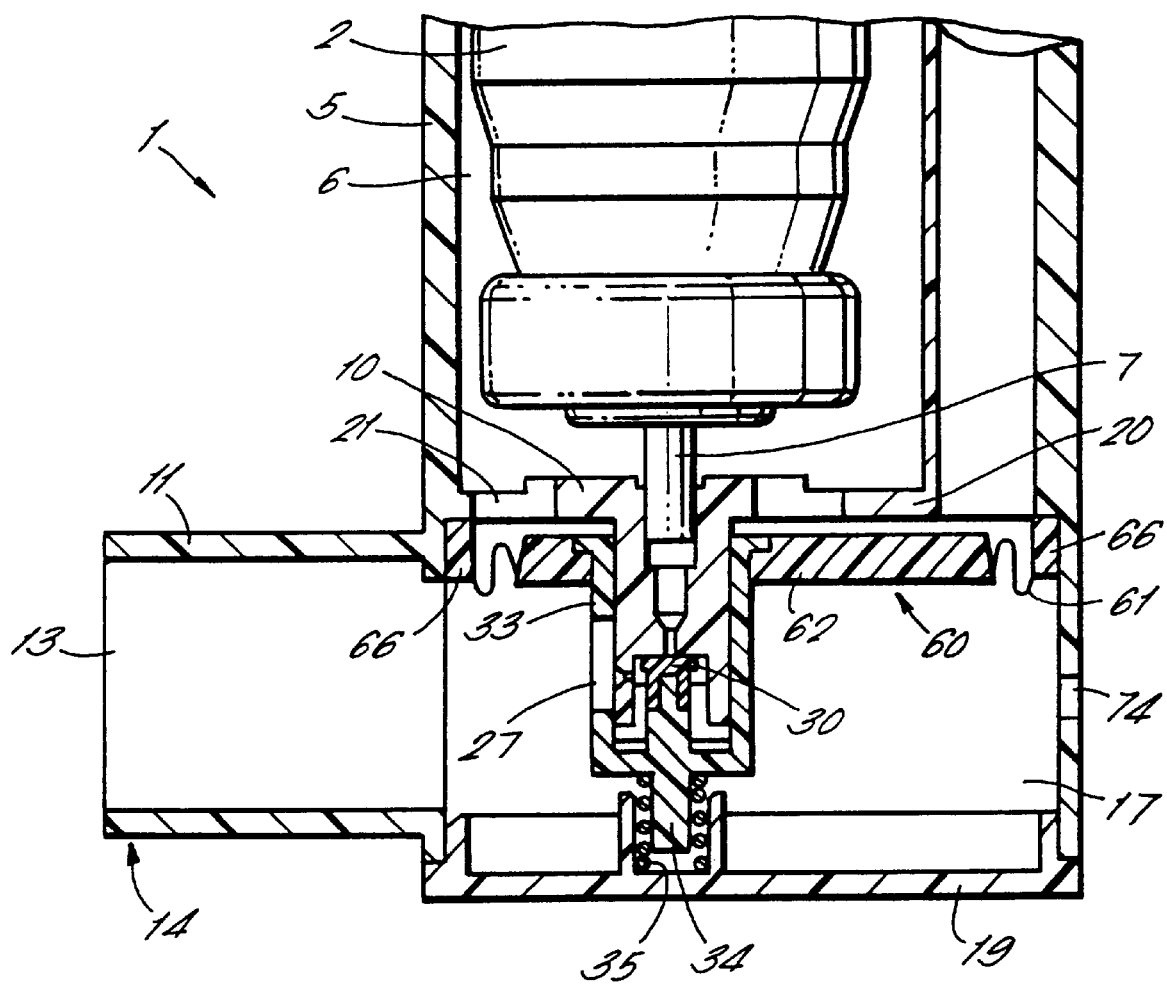
FIG. 8 is a sectional side elevation of a part of the dispensing apparatus in accordance with a second embodiment of the present invention, including a pressurised dispensing container, the apparatus being in a first, non-dispensing position.

FIG. 8 shows a second embodiment of dispensing apparatus according to the present invention. The second embodiment is identical to the first embodiment with the exception that there are no apertures in the second diaphragm element 62. Rather the diaphragm 60 forms an air-tight seal across the housing 4 at the base of the cylindrical portion 5. One or more apertures 74 are instead provided in the housing 4 allowing flow of air between an exterior of the apparatus 1 and chamber 17.

Operation of the apparatus is the same as in the first embodiment. As a user inhales air flows from the exterior of the apparatus through apertures 74 and mouthpiece 11. In the same manner as the first embodiment, the second diaphragm element is subjected to a downward force because of an imbalance of air pressure above and below the diaphragm.

A third embodiment is shown in FIGS. 9 and 10. The apparatus is similar to that of the first embodiment except for the provision of a means for "priming" or test operating the apparatus. A trigger 80 is provided rotatably mounted on a pivot 81 on housing 5. One end 83 of the trigger 80 extends protrudingly through a hole 82 in the housing 5 such that the trigger is accessible from an exterior of the apparatus 1. The other end 84 of the trigger 80 extends into an interior of the apparatus 1 such that it contacts an upper surface of the second diaphragm element 62 when the second diaphragm element is in the non-dispensing position as shown in FIG. 9.

In use, either to prime the dispensing container 2 or test actuate the apparatus 1, the user depresses the dispensing container 2 relative to the housing 5. As in the previous embodiments, a metered dose of pressurised product is dispensed into actuator chamber 36 which is closed off by the actuator valve 28. Then, instead of inhaling, the user presses end 83 of trigger 80. The trigger 80 rotates about pivot 81 such that end 84 moves axially downwards relative to the housing 5. Downward movement of end 84 causes the second diaphragm element 62 to also move downwardly, into the position shown in FIG. 10, operating the actuator valve 28 in the same manner as the previous embodiments to dispense the product as an aerosol.

The trigger means of the third embodiment is equally applicable for use with the apparatus of the second embodiment in which diaphragm 60 does not contain any apertures.

The diaphragm 60 need not be round, as described in the embodiments above, but may be any desired size and shape to fit within a particular size and shape of housing. The diaphragm 60 may be made of any suitable material having the required flexible and resilient characteristics. Such materials include thermoplastic elastomers, for example Hytrel (RTM), and cured elastomers, for example Buna (RTM) N or butyl rubber.

The diaphragm 60 may be manufactured as a single unitary injection moulding, two-piece injection moulding or by assembly of separate components.

What is claimed is:

1. Inhalation apparatus for dispensing a product comprising a housing adapted to receive a pressurized dispensing container, and a mouthpiece, a duct for conveying, in use, product from the container to the mouthpiece, valve means movable between a first position in which the duct is closed and a second position in which the duct is open, and a flow sensor being activatable, by means of an airflow created when a user applies suction to the mouthpiece, to move the valve means into its second position, wherein the flow sensor comprises a diaphragm and the diaphragm and/or housing is provided with at least one aperture, wherein the diaphragm comprises a first element connected to the housing and a second element axially slidably movable relative thereto, the first and second diaphragm elements being connected by a flexible member.

2. Inhalation apparatus as claimed in claim 1, wherein the diaphragm comprises at least one aperture.

3. Inhalation apparatus as claimed in claim 1, wherein the housing comprises at least one aperture.

4. Inhalation apparatus as claimed in claim 1, wherein at least one aperture is provided in the second diaphragm element.

5. Inhalation apparatus as claimed in claim 1, further comprising a trigger extending from an exterior of the apparatus into contact with the diaphragm such that operation of the trigger moves the diaphragm axially.

6. Inhalation apparatus as claimed in claim 5, wherein the trigger is rotatably pivoted on the housing such that one end protrudes through an aperture in the housing and the other end contacts the diaphragm.

7. Inhalation apparatus as claimed in claim 1, further comprising an actuator having a projection, the diaphragm being connected to a tubular guide portion which is axially slidable on a guide surface of the projection to facilitate movement of the diaphragm.

8. Inhalation apparatus as claimed in claim 7, wherein the actuator further defines an actuator chamber, valve seat and outlet nozzle, the tubular guide portion comprising a spigot on which a valve member of the valve means is mounted.

9. Inhalation apparatus as claimed in claim 1, wherein the housing comprises a socket for receiving the pressurized dispensing container, the housing defining at least one port communicating between the socket and the mouthpiece at a location upstream of the diaphragm with respect to the direction of air flow during inhalation.

10. Inhalation apparatus as claimed in claim 1, wherein a pressure drop of between 2.5 and 4 KPA is developed across the diaphragm when an airflow of 50 liters/minute is created by suction on the mouthpiece.

11. Dispensing means comprising inhalation apparatus as claimed in claim 1, in combination with a pressurized dispensing container; said container having a tubular valve stem biased into an extended position and having valve means operable to dispense a metered dose of product through the valve stem when the valve stem is depressed.

* * * * *